United States Patent [19]
Sussman

[11] Patent Number: 6,025,905
[45] Date of Patent: Feb. 15, 2000

[54] SYSTEM FOR OBTAINING A UNIFORM ILLUMINATION REFLECTANCE IMAGE DURING PERIODIC STRUCTURED ILLUMINATION

[75] Inventor: Michael Sussman, Winchester, Mass.

[73] Assignee: Cognex Corporation, Natick, Mass.

[21] Appl. No.: 08/777,107

[22] Filed: Dec. 31, 1996

[51] Int. Cl.$^7$ .............................. G01C 03/00; B25J 19/00
[52] U.S. Cl. .......................... 356/3.01; 901/47; 382/106; 382/154
[58] Field of Search .............................. 348/86, 131, 135; 382/106, 153, 154; 250/559.22; 901/47; 356/376, 394, 3.01

[56] References Cited

U.S. PATENT DOCUMENTS

| | | | |
|---|---|---|---|
| 4,472,056 | 9/1984 | Nakagawa et al. | 356/376 |
| 4,640,620 | 2/1987 | Schmidt | 356/376 |
| 4,689,480 | 8/1987 | Stern | 250/201 |
| 4,755,047 | 7/1988 | Kato et al. | 356/376 |
| 4,876,455 | 10/1989 | Sanderson et al. | 250/560 |
| 4,893,183 | 1/1990 | Nayar | 358/107 |
| 4,912,336 | 3/1990 | Nayar et al. | 250/560 |
| 4,984,893 | 1/1991 | Lange | 356/376 |
| 4,988,202 | 1/1991 | Nayar et al. | 356/394 |
| 5,148,211 | 9/1992 | Kotani et al. | 354/403 |
| 5,151,609 | 9/1992 | Nakagawa et al. | 250/561 |
| 5,239,178 | 8/1993 | Derndinger et al. | 250/234 |
| 5,248,876 | 9/1993 | Kerstens et al. | 250/561 |
| 5,424,835 | 6/1995 | Cosnard et al. | 356/376 |
| 5,434,612 | 7/1995 | Nettleton et al. | 348/31 |
| 5,526,038 | 6/1996 | Lux | 348/29 |
| 5,546,189 | 8/1996 | Svetkoff et al. | 356/376 |
| 5,589,942 | 12/1996 | Gordon | 356/376 |
| 5,617,209 | 4/1997 | Svetkoff et al. | 356/376 |
| 5,621,529 | 4/1997 | Gordon et al. | 356/376 |
| 5,659,420 | 8/1997 | Wakai et al. | 359/368 |

FOREIGN PATENT DOCUMENTS

| | | |
|---|---|---|
| 0 183 240 A2 | 6/1986 | European Pat. Off. . |
| 0 300 164 A1 | 1/1989 | European Pat. Off. . |
| 0 563 829 A2 | 10/1993 | European Pat. Off. . |
| 0 627 610 A1 | 12/1994 | European Pat. Off. . |
| 3413605 A1 | 10/1985 | Germany . |
| 3-63507 | 8/1989 | Japan . |
| 9-26312 | 8/1989 | Japan . |
| 4-283608 | 3/1991 | Japan . |
| 4-313008 | 4/1991 | Japan . |
| 6-249632 | 2/1993 | Japan . |
| 7-311025 | 5/1994 | Japan . |
| 8-233544 | 2/1995 | Japan . |
| 9-5046 | 6/1995 | Japan . |
| 8-152308 | 9/1995 | Japan . |
| 8-304043 | 9/1995 | Japan . |
| 9-96512 | 9/1995 | Japan . |
| 9-127420 | 11/1995 | Japan . |
| WO 96/41304 | 12/1996 | WIPO . |

OTHER PUBLICATIONS

A. Pentland, S. Scherock, T. Darrell, and B. Girod. "Simple range cameras based on focal error," J. Opt. Soc. Am. A., vol. 11, No. 11, Nov. 1994, pp. 2925–2934.

(List continued on next page.)

*Primary Examiner*—Mark Hellner
*Attorney, Agent, or Firm*—Russ Weinzimmer

[57] ABSTRACT

The invention provides an apparatus and method for obtaining a uniform illumination reflectance image of an object, even though the object is illuminated only using periodic structured illumination. The uniform illumination reflectance image so-produced has precise geometric and photometric correspondence with images produced using the periodic structured illumination. To obtain the uniform illumination reflectance image, a sum of a spanning set of periodic structured illumination images is computed. The resulting summation image bears substantially no trace of periodic structured illumination. Various embodiments of the apparatus of the invention are disclosed employing illuminator motion, object motion, and ray deflection to obtain a plurality of periodic structured illumination images of different phase. The invention is useful with triangulation ranging systems using a striped periodic illumination mask, with depth-from-focus ranging systems, and with depth-from-defocus ranging systems.

28 Claims, 9 Drawing Sheets

OTHER PUBLICATIONS

B. Girod, and S. Scherock "Depth from Defocus of Structured Light," SPIE vol. 1194 Optics, Illumination, and Image Sensing for Machine Vision IV (1989), pp. 209–215.

P. Caber, "Interferometric profiler for rough surfaces," Applied Optics, vol. 32, No. 19, Jul. 1 1993, pp. 3438–3441.

S. Nayar and Y. Nakagawa, "Shape from Focus," IEEE Transactions on Pattern Analysis and Machine Intelligence, vol. 16, No. 8, Aug. 1994, pp. 824–830.

Y. Xiong and S. Shafer, "Depth from Focusing and Defocusing," Proc. IEEE Conference on Computer Vision and Pattern Recognition 1993, pp. 68–73.

J. Wyant, "How to extend interferometry for rough surface tests," Laser Focus World, Sep. 1993, pp. 131–133.

J.-A. Beraldin, M. Rioux, F. Blais, and R. A. Couvillon, "Digital Three–dimensional Imaging in the Infrared at the National Research Council of Canada," SPIE vol. 2269 Infrared Technology XX (1994), pp. 208–225.

Z.J. Geng, "Rainbow three–dimensional camera: new concept of high–speed three–dimensional vision systems," Optical Engineering, vol. 35 No. 2, Feb. 1996, pp. 376–383.

M. Watanabe and S. Nayar, "Telecentric Optics for Constant–Magnification Imaging," Technical Report CUCS–026–95, Dept. of Computer Science, Columbia University, New York, NY, USA, Sep. 1995.

M. Watanabe, S. Nayar, and M. Noguchi, "Active Focus Range Sensor," Implementation Technical Note, Dept. of Computer Science, Columbia University, New York, NY, USA, Jun. 1995.

M. Watanabe, S. Nayar, and M. Noguchi, "Real–time computation of depth from defocus," Proc. of SPIE v 2599, 1996, pp. 14–25.

S. Nayar, M. Watanabe, and M. Noguchi, "Real–Time Focus Range Sensor," IEEE Transactions of Pattern Analysis and Machine Intelligence, vol. 18, No. 12, Dec. 1996, pp. 1186–1198.

M. Noguchi and S. Nayar, Microscopic Shape from Focus Using Active Illumination, Proc. IEEE Conference on Computer Vision and Image Processing 1994, pp. 147–152.

M. Subbarao and G. Surya, "Depth from Defocus: A Spatial Domain Approach," International Journal of Computer Vision, 13, 3, 1994, pp. 271–294.

R. Stone and S. Shafer, "Surface Roughness Estimation," The Robotics Institute, Carnegie Mellon University, Pittsburgh, PA, USA.

A. Pentland, "A New Sense for Depth of Field," IEEE Transactions on Pattern Analysis and Machine Intelligence, vol. PAMI–9, No. 4, Jul. 1987, pp. 523–531.

M. Ishihara and H. Sasaki, "High Speed 3–D Shape Measuring Apparatus using Shape from Focus Method," Seimitsu Kogaku Kaishi (Precision Engineering Journal), No. 63, No. 1, 1997, pp. 124–128.

"Confocal Microscopy," Optical Instruments, pp. 17.40–17.43.

R. Webb, "Confocal Microscopes," Optics & Photonics News, Jul. 1991, pp. 8–13.

R. Schneider, A. Schick, P. Kollensperger, and T. Ninomiya, "High–speed optical three–dimensional scanner for automatic solder joint inspection," Optical Engineering, vol. 36, No. 10, Oct. 1997, pp. 2878–2885.

M. Ishihara, "High Speed 3–D Shape Measurement for a Small Object," Dai Ni–kai Gazou Senshing Shinpojiumu Kouen Ronbunshuu (Collection of the Lectures at the 2nd Image Sensing Symposium), Jun. 1996, pp. 155–158.

M. Ishihara and H. Sasaki, "High Speed 3–D Shape Measurement Using Non–Scanning Multibeam Confocal Lens System," Dai San–kai Gazou Senshing Shinpojiumu Kouen Ronbunshuu (Collection of the Lectures at the 3rd Image Sensing Symposium).

T. Yamashita and H. Nakashima; M. Nagashima and K. Nishiuchi, "Measuring longitudinal displacements using laser beam diffraction changes near the focal point," Rev. Sci. Instrum., vol. 64, No. 8, Aug. 1993, pp. 2245–2249.

Patent Abstracts of Japan, vol. 8, No. 6 (P–247) '1443!, Jan. 12, 1984 & JP 58 169008 A (Nippon Denki K.K.), Oct. 5, 1983.

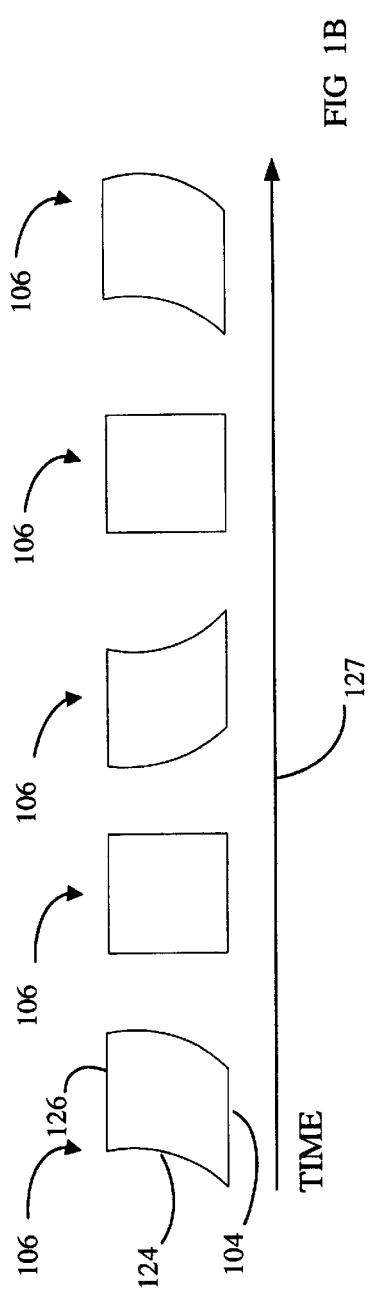
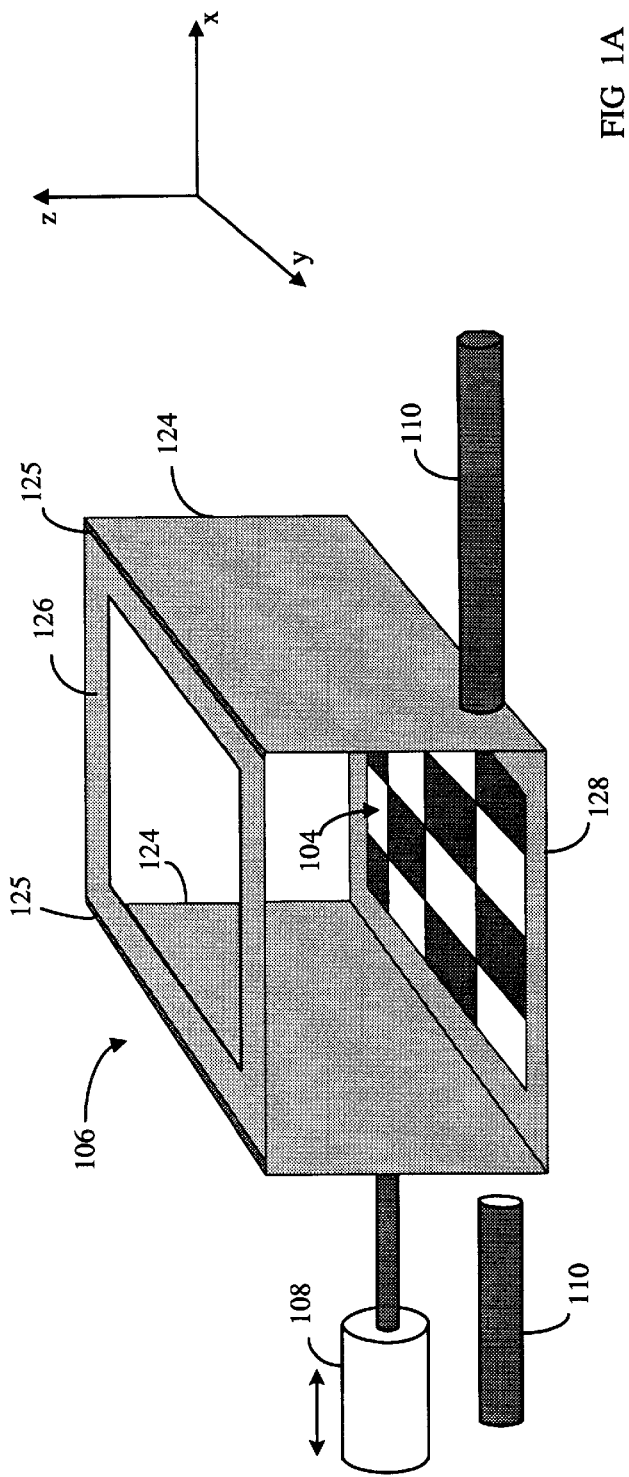

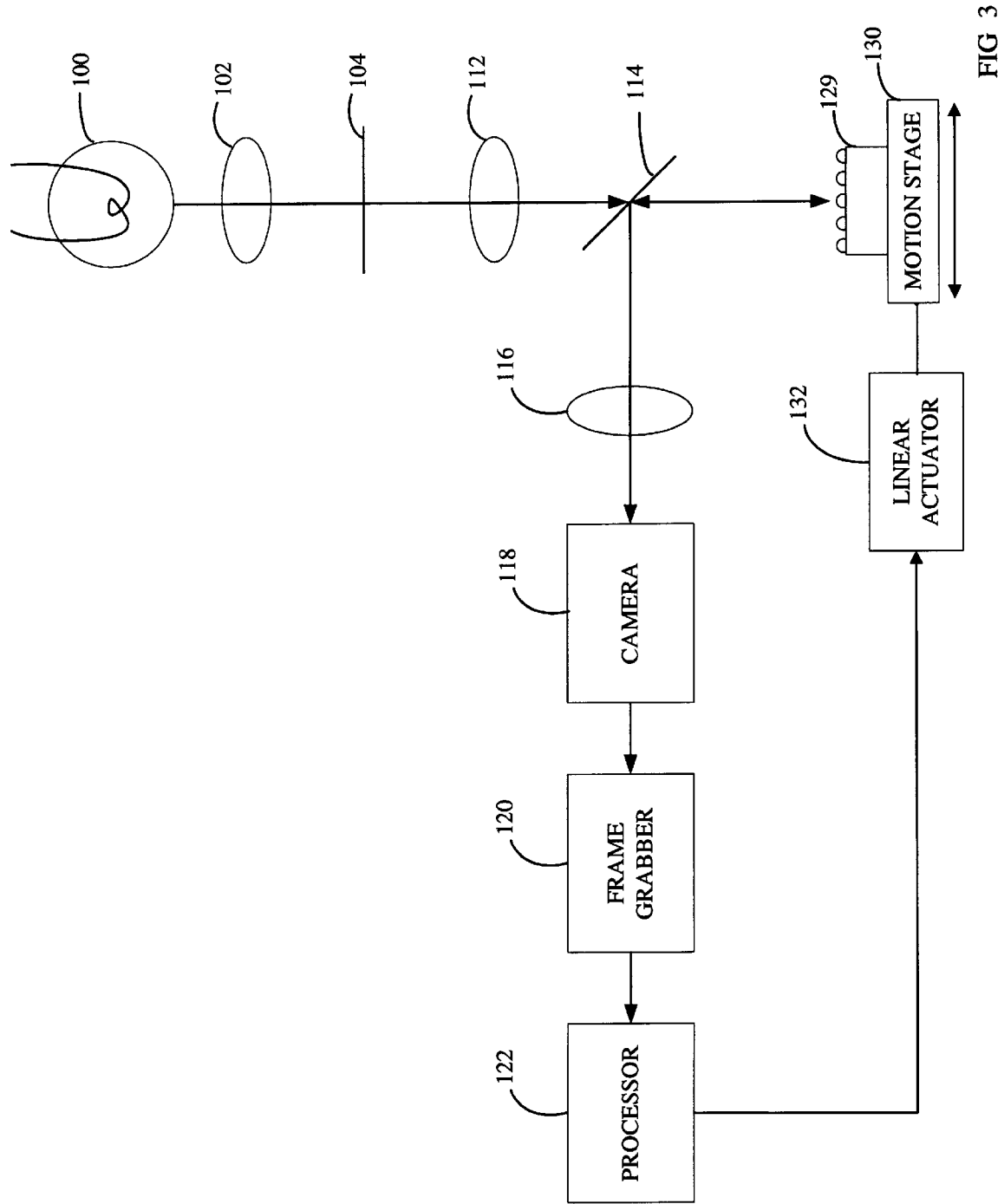

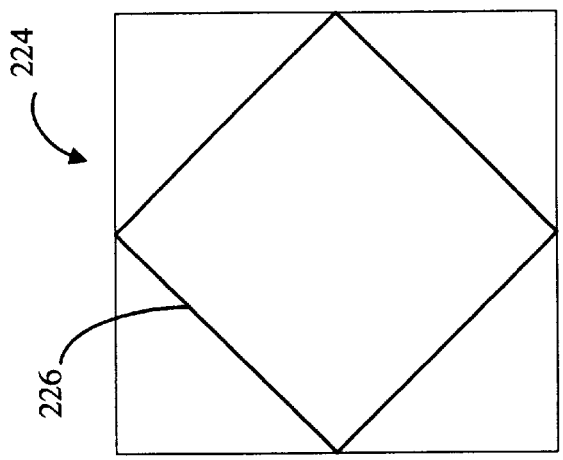
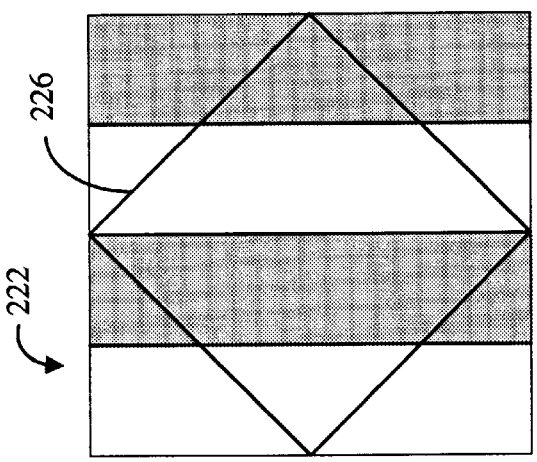
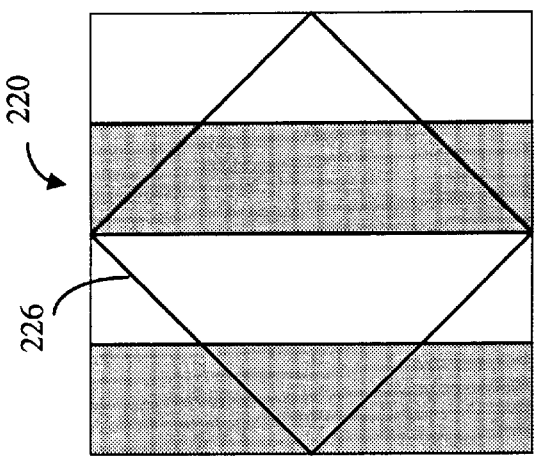
FIG 6

SYSTEM FOR OBTAINING A UNIFORM ILLUMINATION REFLECTANCE IMAGE DURING PERIODIC STRUCTURED ILLUMINATION

FIELD OF THE INVENTION

This invention relates generally to machine vision, and particularly to machine vision applications that employ periodic structured illumination.

BACKGROUND OF THE INVENTION

Structured illumination is a lighting technique used in machine vision, one application being to optically recover object shape information. For example, in Horn, *Robot Vision*, MIT Press, 1986, p. 95, a system is described that uses a "sheet" of light and a CCD camera to triangulate a plurality of surface locations of an object to produce a range image. A range image is an image wherein each pixel represents a perpendicular distance from a corresponding point on the surface of an object to a reference plane, e.g., a depth or a height.

"Laser light striping" is a method of structured illumination that is commonly used to obtain range images using such triangulation methods. In laser light striping, periodic, i.e., repeating stripe patterns of illumination are used. For high speed image acquisition, area array cameras are used.

Liquid crystal display (LCD) light projectors are also used in periodic light stripe triangulation, since the pattern position or period can be altered electronically to produce higher resolution images. See, for example Sato and Inokuchi, "Range-imaging System Utilizing Nematic Liquid Crystal Mask", Proceedings of the First International Conference on Computer Vision, p 657–661, IEEE Comp. Soc. Press, 1987, which discloses the use of complementary projected patterns for binarizing an input image.

In M. Rioux and F. Blais, "Compact three-dimensional camera for robotic application". J. of Optical Soc. of America A, 3(9):1518–1521, September 1986, a different method of object ranging is disclosed that uses a structured illuminator which projects an array of dots. The illumination pattern is projected onto an object, which is viewed by an area array CCD camera. Range information is recovered at each dot location using the extent of defocus of the dot, as measured by the diameter of the defocused image of the dot. Rioux's method is a precursor of a family of "depth from focus" and "depth from defocus" methods which do not use triangulation. The methods in this family all employ the focal characteristics of a lens to determine surface range by measuring local image sharpness or local image blur. These methods may also use structured illumination having a fine periodic pattern to force texture onto otherwise uniformly reflective objects. In the case of depth from defocus, as disclosed in M. Watanabe, S. K. Nayar, and M. Noguchi, "Real-time Computation of depth from defocus". Proc. of the SPIE, vol 2599:A-03, p. 14–25, November 1995, the known spatial frequency content of periodic structured illumination has been exploited to simplify computation of degree of defocus, i.e., blur, in an image.

In machine vision, it can be advantageous to obtain both a normal reflectance image of an object, and a corresponding range image of the object. For example, when inspecting solder balls on ball grid array (BGA) semiconductor packages, it can be preferable to locate ball center positions by machine vision analysis of a reflectance image of the solder balls. Ball center heights can then be gauged at each found ball center position using the corresponding range image of the solder balls. Due to the three-dimensional nature of the objects being inspected, it is important that the angle of illumination and angle of viewing be the same when producing the reflectance and range images. If the angle of illumination is not the same, shadowing and shading will create differences in image brightness, herein termed "photometric non-correspondence". In the BGA inspection example above, shadows can shift the ball center position found in analysis of the reflectance image, resulting in position measurement error. This will cause ball height to be gauged in the wrong position of the range image of the example. Moreover, if the angle of viewing is different, surface relief will create displacements of object features between the two images, herein termed "geometric non-correspondence". In the BGA inspection example above, displacement of object features between the two images can result in correspondence errors, resulting again in errors in determining height from the height image.

Some machine vision applications require both exact geometric correspondence and exact photometric correspondence between a uniform illumination reflectance image and a structured illumination reflectance image, such as when a reflectance image and a range image must be compared, because the range image is derived from the structured illumination reflectance image. This comparison requires that the structured and reflectance images are precisely registered, i.e., geometric correspondence is required, and requires that the illumination conditions are substantially identical except for the structuring component, i.e., substantial photometric correspondence is required.

One method for obtaining images under a mixture of structured and uniform illumination uses two light sources: a structured illuminator and an unstructured illuminator. However, photometric correspondence is very difficult to obtain using this illumination approach. If the two illuminators are mounted side-by-side, i.e., not in coaxial relationship, the consequent small difference in angular displacement of the illuminators results in significant differences in object shading. A coaxial arrangement of the illuminators can be achieved using a half-silvered mirror (beam splitter) that combine the two light sources so as to substantially remove gross angular discrepancies. However, using a coaxial arrangement will not provide photometric correspondence if the illuminator efficiency of the structured illuminator and the illuminator efficiency of the uniform illuminator are different, resulting in photometric non-correspondence. Further, it is very difficult to make a highly uniform illuminator, i.e., an illuminator that provides illumination uniformly over the entire cross-sectional area of its illumination beam, and non-uniformity of one illuminator will generally not match the non-uniformity of a second illuminator. This phenomena also contributes to photometric non-correspondence.

Alternatively, it is possible to take an image acquired under structured illumination and electronically filter out the structured illumination component to obtain a uniform illumination reflectance image. However, the resulting image will have a resolution which is limited by the frequency characteristics of the filter. Consequently, the structured and unstructured illumination images will exhibit photometric non-correspondence on object features with image components of high spatial frequency, such as step edges.

Other methods can be described for obtaining both uniform illumination reflectance images and structured illumination reflectance images of an object, but difficulties remain in obtaining such images in a practical and economical manner that also exhibit precise geometric and photometric correspondence.

SUMMARY OF THE INVENTION

The invention provides an apparatus and method for obtaining a uniform illumination reflectance image of an object, even though the object is illuminated only using periodic structured illumination. Moreover, the uniform illumination reflectance images so-produced have precise geometric and photometric correspondence with images produced using the periodic structured illumination.

According to the invention, the uniform illumination reflectance image is assembled from a plurality of periodic structured illumination reflectance images, where the phase of the periodic structured illumination of each image is different, and the period of the periodic structured illumination of each image is the same. To obtain the uniform illumination reflectance image, a sum of a spanning set of periodic structured illumination images is computed. The resulting summation image bears substantially no trace of periodic structured illumination, the periodic structured illumination being effectively removed by interlocking assembly of the spanning set of periodic structured illumination images to provide a substantially uniform illumination reflectance image.

Further, the method of the invention provides a uniform-illumination reflectance image, in a system employing periodic structured illumination, that is characterized by both substantial geometric correspondence and substantial photometric correspondence with at least one captured periodic structured illumination image. The method first generally employs the step of capturing a first periodic structured illumination image of the object to provide a first captured periodic structured illumination image characterized by a period and a first phase. Next, a second periodic structured illumination image of the object is captured so as to provide a second captured periodic structured illumination image characterized by a second phase and by a period that is substantially identical to the period of the first captured periodic structured illumination image. Then, at least the first captured periodic structured illumination image and the second captured periodic structured illumination image are combined so as to provide a substantially uniform-illumination reflectance image that is characterized by both substantial geometric correspondence with at least one of the captured periodic structured illumination images, and substantial photometric correspondence with the at least one of the captured periodic structured illumination images.

In general, where the spanning set of periodic structured illumination images has more than two members, the second phase is different from the first phase. When there are only two periodic structured illumination images, it is preferable that the second phase is in 180 degree phase relationship with the first phase.

The invention can be applied to periodic structured illumination systems employing both one-dimensional (light stripe) and two-dimensional periodic structured illumination patterns. Various embodiments of the apparatus of the invention are shown employing illuminator motion, object motion, and ray deflection to obtain a plurality of periodic structured illumination images of different phase.

The invention has utility in any method or apparatus that uses a periodic mask, where the mask image component is to be removed from a reflectance image formed using the periodic mask. For example, the invention is useful with triangulation ranging using a striped periodic illumination mask, depth-from-focus ranging, and depth-from-defocus ranging.

The invention avoids the need to use a separate illumination source and separate projection optics for creating a uniform illumination reflectance image, and thereby avoids the problems inherent therein regarding the likely non-matching non-uniformity of the additional illumination source and projection optics. This is accomplished by using the same illumination source and projection optics for obtaining both structured illumination and uniform illumination reflectance images.

BRIEF DESCRIPTION OF THE DRAWINGS

The invention will be more fully understood from the following detailed description, in conjunction with the accompanying figures, wherein:

FIG. 1A is a perspective view of the flexure mechanism of FIG. 1;

FIG. 1B is an animated sequence of the flex motion of the flexure mechanism of FIG. 1A;

FIG. 3 is a schematic representation of a preferred embodiment of the invention that employs object motion;

FIG. 6 is an illustration of the addition of two different stripped structured illumination images of an object to provide a uniform illumination image of the object.

DETAILED DESCRIPTION OF THE FIGURES

Figure 1:
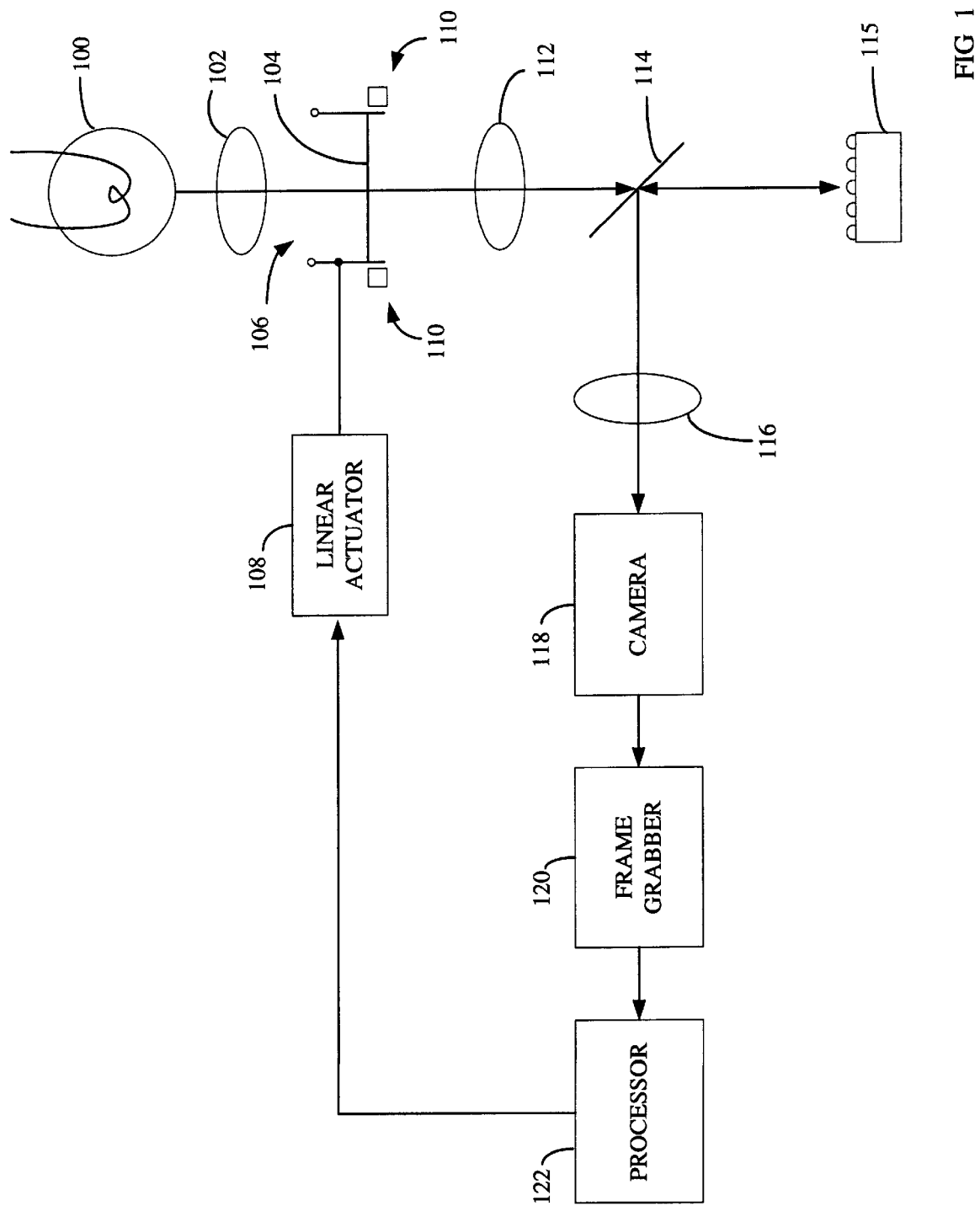
FIG. 1 is a schematic representation of a preferred embodiment of the invention that employs illuminator mask motion.

With reference to FIG. 1, light from an illumination source, such as a lamp 100, is collimated by a lens 102 onto a periodic pattern mask 104 for providing structured illumination. The mask 104 is preferably fabricated from a glass plate with a periodic chrome pattern composed of substantially opaque and transparent regions, for example. The mask 104 can be fabricated using the same photolithographic process as used in making masks for integrated circuit manufacturing.

Figure 2:
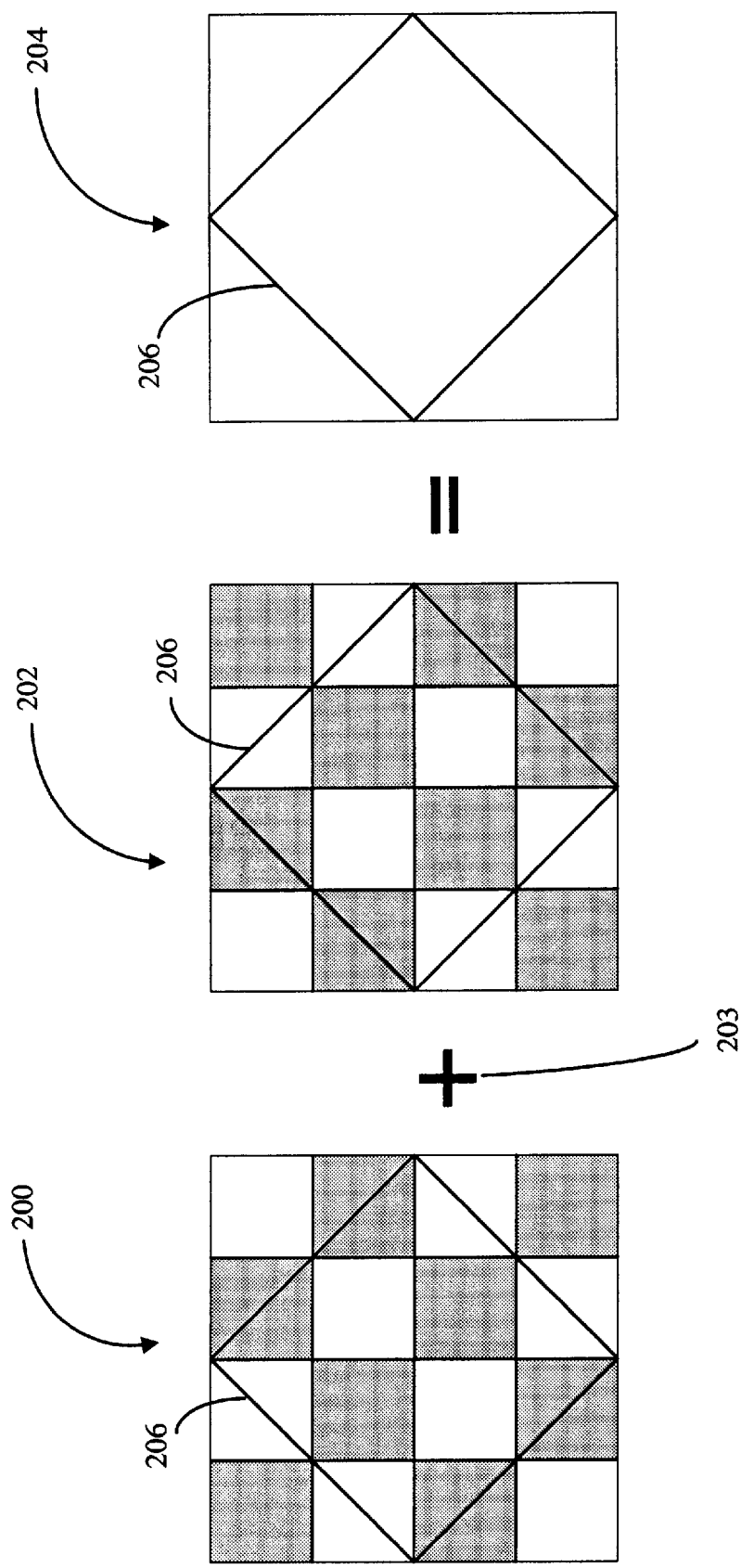
FIG. 2 is an illustration of the addition of two different structured illumination images of an object to provide a uniform illumination image of the object.
Figure 2A:
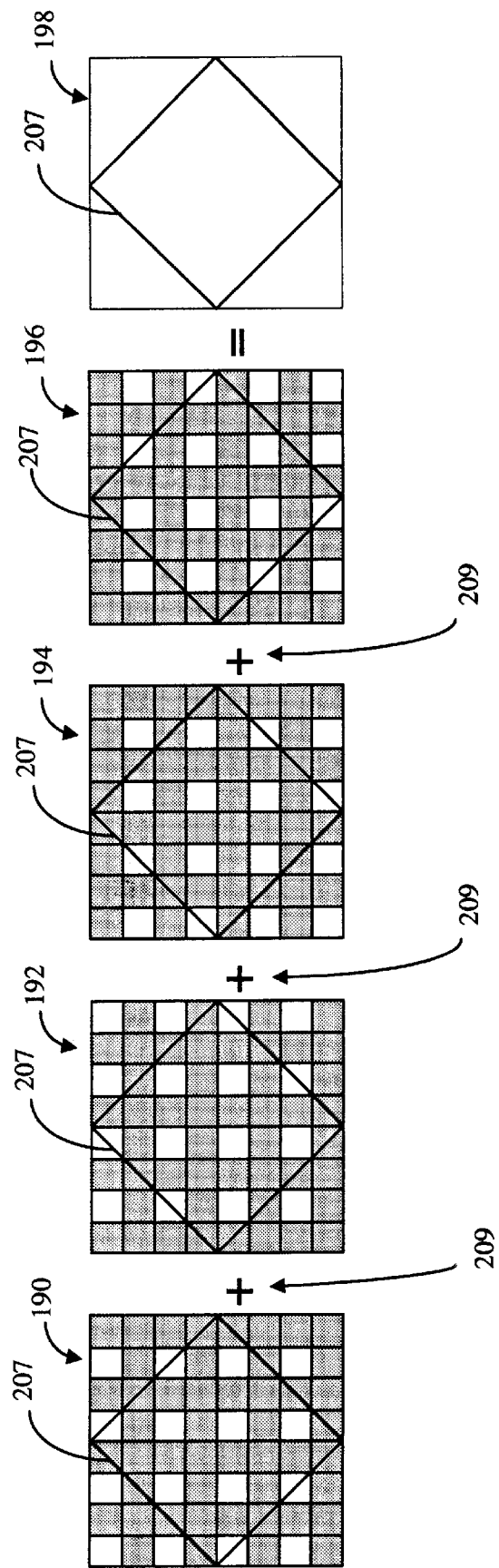
FIG. 2A is an illustration of the addition of four different structured illumination images of an object to provide a uniform illumination image of the object.

The mask 104 is mounted such that it can be moved into a plurality of different positions so as to create a "spanning set" of mutually orthogonal structured illumination patterns. Three example spanning sets are shown in FIGS. 2, 2A, and 6, having two, four, and two patterns, respectively. Each structured illumination pattern of the spanning set is of a different phase along at least one dimension. It is a defining property of the spanning set that the sum of all of the patterns in the set results in substantially uniform unstructured illumination, as illustrated in FIGS. 2, 2A, and 6.

In a preferred embodiment, the mask 104 is mounted on a flexure mechanism 106, shown in detail in FIG. 1A, that permits only lateral (side-to-side) movement. In other embodiments, such as an embodiment that results in the spanning set of periodic structured illumination patterns shown in FIG. 2A, both side-to-side and front-to-back movement (two degrees of freedom) are possible. The flexure mechanism 106 acts as a carriage for the mask 104, and is substantially rigid in the y-dimension and the z-dimension (up and down, and forward and back), while being flexible only in the x-dimension (side-to-side). The flexure mechanism 106 consists simply of two flat springs 124 affixed at one end to a transparent square frame 126, and at the other end to a carrier frame 128 that supports the mask 104. The transparent square frame 126 is affixed to a rigid support (not shown) via the braces 125.

A linear actuator 108, preferably a piezo-electric element, is linked to the mask 104 via the flexure mechanism 106. When energized, the linear actuator 108 moves the mask 104 one half of the period of the illumination pattern, the linear motion of the mask 104 being bounded by the location of the hard motion stops 110. The two mask positions separated by one half of the illumination pattern period provides a complete spanning set of structured illumination patterns, thereby permitting assembly of a reflectance image, as described below in conjunction with FIG. 2.

The motion of the flexure mechanism 106 is depicted in the animated sequence of FIG. 1B. The time arrow 127 indicates that as time passes, the flexure mechanism moves the mask 104 from side to side.

Light passing through the mask 104 is collected by a lens 112 and projected through a beam splitter 114 onto an object 115 to be imaged. The mask 104 is located with respect to lens 112 such that the mask pattern of the mask 104 is projected in focus onto the object 115. Light reflected from of the object is reflected by the beam splitter 114, and is then collected by a viewing lens 116. The beam splitter 114 is here used to provide coaxial illumination and viewing of the object 115 so as to eliminate shadow effects, but is not essential to the invention.

Light collected by the lens 116 is focused towards a camera 118, preferably a camera that includes a CCD image sensor. The images captured by the camera 118 are digitized and then stored in the memory of a frame grabber 120. A processor 122, preferably a personal computer, is used to process an entire spanning set of images. The images of the spanning set are generally produced, each with a different phase, by moving the mask 104. When the spanning set of FIG. 2 is used, wherein each of the two structured illumination patterns is shifted by 180 degrees with respect to the other pattern, the two patterns are produced by moving the mask 104 between two positions, as determined by the motion stops 110.

FIG. 2 is an illustration of the process of mask pattern cancellation by adding a plurality of images created by illuminating an object using a spanning set of periodic structured illumination patterns, thereby providing uniform illumination reflectance image assembly. The structured illuminator mask 104 is here preferably a checkerboard pattern, the effect of which, when used to illuminate an object 206, is to create a first acquired structured illumination image 200. Acquired image 200 also shows the reflectance of the viewed object 206. (An actual mask will have many more pattern cycles than that shown schematically in the FIGS. 2, 2A, and 6.)

When the mask 104 is physically shifted with respect to the object 206 and the camera 118 by one-half of its period (180 degrees of phase), the object 206 is illuminated with the pattern, and an image thereof is captured, the second acquired structured illumination image 202 results. For example, if the mask period (one illuminated square and one dark square) is 100 μm, then the mask will be shifted by 50 μm to produce the needed phase shift. Note that, due to the particular lattice properties of the mask 104, moving the mask along only one axis creates a 180 degree phase shift along both major directions (x and y) of the mask pattern. After the phase shift, a location on the illuminated object 206 which previously fell on a dark region of the projected mask pattern 200 will fall on a bright region for shifted mask pattern 202. Note that all regions of the object 206 are illuminated either by the mask position providing the pattern 200 or the pattern 202. Thus, if an image is acquired at each discrete mask position, then the sum of the two images, the addition operation being denoted by reference number 203 in FIG. 2, will result in a uniform illumination image 204 that nowhere shows the projected periodic structured illumination mask pattern.

Stated more formally, if A represents the first image 200, and B represents the second image 202 with the mask 104 shifted by half a period, then R is a uniform illumination reflectance image 204, wherein each image A, B, and R is a two dimensional image having a plurality of pixels, each pixel being specified by a pair of image coordinates (x, y):

$$R(x,y) = A(x,y) + B(x,y) \qquad \text{Equation 1}$$

The reflectance image R(x,y) so-produced will be photometrically equivalent to an image taken with no mask pattern at all. Further, as recognized by the invention, the reflectance image R(x,y) so-produced will be photometrically equivalent to each of the images A(x,y) and B(x,y). Thus, the invention provides a method and apparatus for obtaining a reflectance image R(x,y) that is photometrically equivalent to each of the periodic structured illumination images that are used to obtain the reflectance image R(x,y).

Moreover, the reflectance image R(x,y) so-produced will be geometrically equivalent to an image taken with no mask pattern at all. Additionally, as recognized by the invention, the reflectance image R(x,y) so-produced will be geometrically equivalent to each of the images A(x,y) and B(x,y). Thus, in general, the invention provides a method and apparatus for obtaining a reflectance image R(x,y) that is geometrically equivalent to each of the periodic structured illumination images that are used to obtain the reflectance image R(x,y).

Obtaining a reflectance image R(x,y) that is both geometrically and photometrically equivalent to each of the periodic structured illumination images that are used to obtain the reflectance image R(x,y) is useful whenever such non-equivalence would be problematic, such as when a reflectance image and a range image must be compared.

If instead we wish to have a reflectance image $R_{EQ}(x,y)$ with average brightness over the entire image equal to the average brightness over the entire structured illumination image A(x, y), the average illumination is computed when combining pixels in images A(x,y) and B(x,y):

$$R_{EQ}(x,y) = (A(x,y) + B(x,y))/2 \qquad \text{Equation 2}$$

or, in the general case of a spanning set of n periodic structured illumination images:

$$R_{EQ}(x,y) = (A(x,y) + B(x,y) + C(x,y) + \ldots)/n \qquad \text{Equation 3}$$

The above image processing operations are performed using the processor 122 of FIG. 1.

Another example of a spanning set of periodic structured illumination patterns is provided in FIG. 2A, wherein a spanning set of four orthogonal periodic structured illumination patterns is used to create four structured illumination images 190, 192, 194, 196 of an object 207. A summation operation 209 is performed using the processor 122 to obtain the uniform reflectance image 198.

FIG. 6 shows a one-dimensional example of a spanning set of periodic structured illumination patterns. FIG. 6 also shows the application of the invention to a striped periodic illumination pattern of the type used in triangulation-based range imaging systems. An image 220 is a first image of an object 226 based on a first mask phase, and an image 222 is a second image created using a second mask phase that is phase shifted by 180 degrees with respect to the first mask phase. An image 224 is a uniform illumination reflectance image formed by the sum 223 of images 220 and 222, as in FIGS. 2 and 2A. The mask shift embodiment of FIG. 1, moving-object embodiment of FIG. 3, or image displacement embodiment of FIG. 5 can each be used with a striped periodic mask according to the invention.

It will be recognized by those skilled in the art that many other mechanical, electromechanical, and electro-optic arrangements, such as liquid crystal arrangements and light valves, can be used to produce the needed motion or apparent motion of the mask 104 without departing from the invention.

FIG. 3 depicts a second preferred embodiment of the invention. As in FIG. 1, light from illuminator 100 is collimated by the lens 102 and passed through the periodic structured illumination pattern mask 104. Here., the mask 104 is rigidly mounted. The pattern of the mask 104 is projected by the lens 112 through the beam splitter 114, and is then focused onto the object 129. The object 129 is placed on top of a translation stage 130, which is operated by a linear actuator 132. Light reflected from the object 129 is reflected by the beam splitter 114 towards the viewing lens 116, the viewing lens 116 focusing the light onto the image sensor of the camera 118. The images captured by the camera 118 are digitized and then stored in memory by the frame grabber 120. The processor 122 then processes pairs, or generally sets, of images, in accordance with the equations set forth above.

In FIG. 3, the object is moved to create an orthogonal spanning set of periodic structured illumination patterns, instead of moving the mask, as described in conjunction with FIG. 1. Using the mask patterns of FIGS. 2 and 6, for example, the motion required is a movement that provides a 180 degree phase shift in the mask pattern at the object 129. Note that the size of the mask pattern at the object must be considered when determining the required amount of shifting of the object. For example, if the mask 104 has a 100 $\mu$m period, and the projection lens 112 has a magnification of two times, then the mask period will be 200 $\mu$m when observed at the object. Consequently, in this example, the required shift will be 100 $\mu$m.

Figure 4:
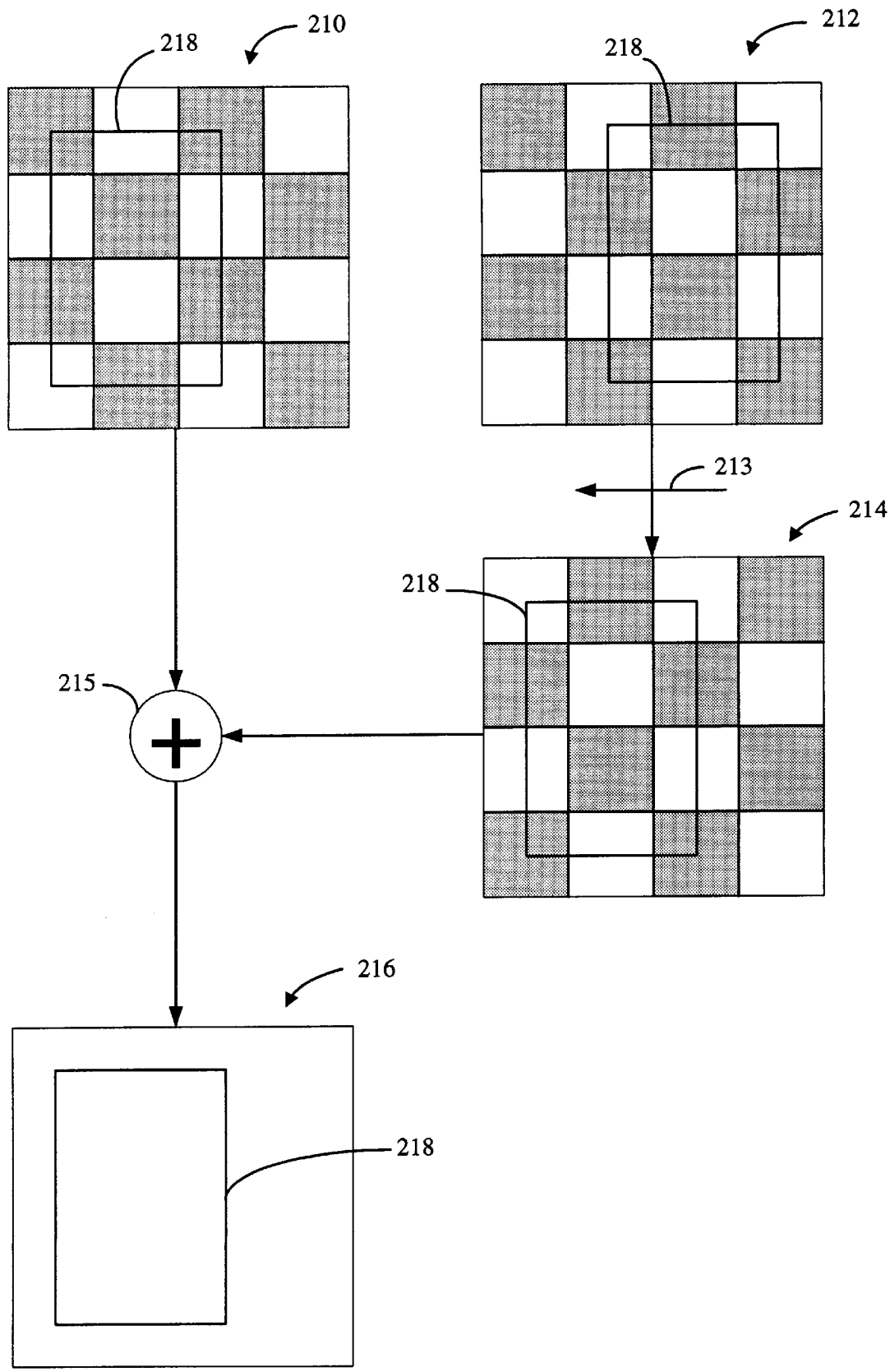
FIG. 4 is an illustration of the addition of two different structured illumination images of an object, via an intermediate shifted image, to provide a uniform illumination image of the object.

FIG. 4 is a schematic representation of the process of mask pattern cancellation for uniform illumination reflectance image assembly with the moving object embodiment of FIG. 3. The "checkerboard" pattern of the mask 104 is evident in the image 210 of the object 218 acquired at an initial object position, and a shifted version of the checkerboard pattern is evident in the image 212 of the object 218 acquired at a second object position. Note that although the structured illumination pattern has shifted with respect to the object 218, the object 218 has also shifted with respect to the camera. To correctly register the images 210 and 212 so that they may be combined to provide a uniform reflectance image of the object 218, it is necessary to shift the second image 212 using a shifting operation 213 so as to produce a shifted image 214. Thus, the effect of the image shifting operation 213 is to shift the phase of the structured illumination pattern, leaving the image of the object 218 is an unchanged position with respect to the first image 210. The images 210 and 214 are then summed 215 to provide the composite image 216, which image is substantially the equivalent of a uniform illumination reflectance image of the object 218.

$$R_{EQ}(x,y)=(A(x,y)+B(x+n,y))/2 \qquad \text{Equation 4}$$

In equation 4, A(x,y) represents the first image 210, B(x+n,y) represents the second image 212 with object 218 shifted, where n is the number of image pixels that the object is displaced in the image, and $R_{EQ}$(x,y) is a uniform illumination reflectance image 216. For example, if the projected mask pattern is viewed (sampled) by the image sensor (CCD) of the camera 118 at four pixels per period, then shift n will be ½ of the period, i.e., two pixels. Note that shifted image 214 is not actually computed. Instead, the needed shift is produced by summing pixels fetched from memory locations in the processor 122 which are linearly displaced by n pixels. The equation produces an image REQ with average brightness over the entire image equal to the average brightness over the entire structured illumination image A. As before, averaging can be omitted if a reflectance image equivalent in overall brightness to the no-pattern condition is desired. The above image processing operations are easily performed using the processor 122 of FIG. 3.

Thus, results obtained using object shifting as shown in FIGS. 3 and 4 are exactly the same as if the mask were shifted, as in FIGS. 1 and 2. In many machine vision applications, precise object translation capability is already available in the form of a robot arm or transport mechanism. The embodiment of FIG. 3 can be used when translation means are already present to provide a more economical system.

Figure 5:
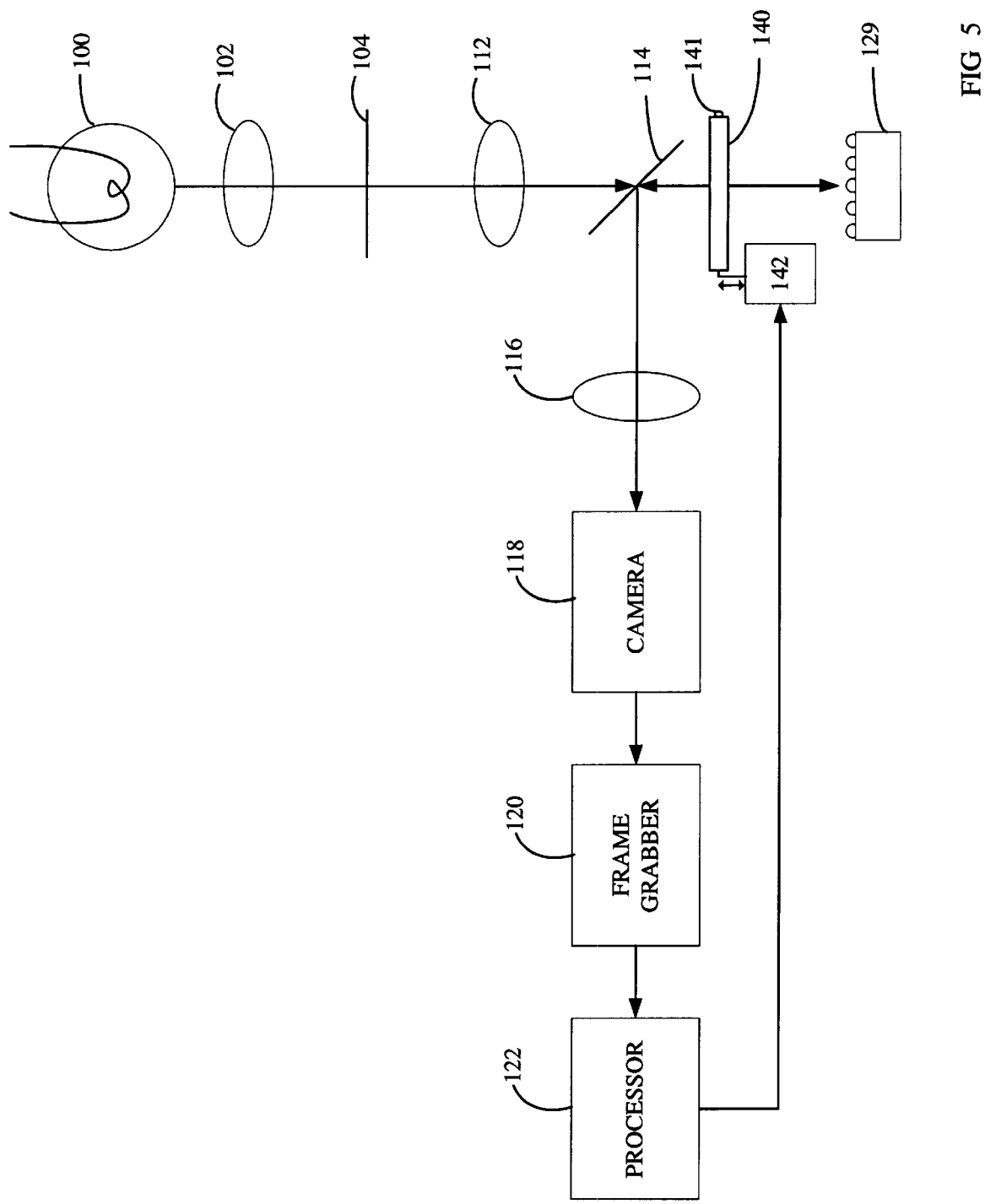
FIG. 5 is a schematic representation of a preferred embodiment of the invention that employs image deflection.

FIG. 5 shows a preferred embodiment of the invention. All of the elements shown in FIG. 5 are identical to the elements shown in FIG. 3, except that the object translation stage 130 and the actuator 132 of FIG. 3 are replaced by a glass plate 140 and linear actuator 142 for tilting the glass plate 140. The glass plate 140 is hingedly affixed via a hinge mechanism 141 to a support member (not shown) so that a linear motion of the actuator 142 can induce a tip in the glass plate 140. The tip can occur in the side-to-side direction and/or the front-to-back direction. As is understood in elementary optics, a tipped transparent plate will create a net image displacement, without changing the angle of the light rays that traverse the plate. Thus, moving the plate 140 by the actuator 142 from a level to a tipped orientation causes a precise displacement of both the projected structured illumination pattern and of the camera field of view. It will be readily appreciated that these displacements are exactly equivalent to those obtained in FIG. 3 wherein the object is moved to achieve periodic structured illumination pattern displacement, and that the images obtained are exactly as in FIG. 4. Thus, image processing required to produce a uniform illumination reflectance image is exactly as in that described in conjunction with FIGS. 3 and 4.

Alternately, electronic projection of structured illumination, for example by using an LCD projector, permits shifting the structuring pattern electronically. A uniform illumination reflectance image is reconstructed from one-dimensional or two-dimensional spanning sets of orthogonal images according to the principles of the invention.

It will be appreciated that other optical, electro-optical, and/or mechanical arrangements and systems are possible which produce spanning set of orthogonal structured illumination patterns which may be used to obtain an unstructured uniform illumination reflectance image without departing from the scope of the invention.

Figure 7:
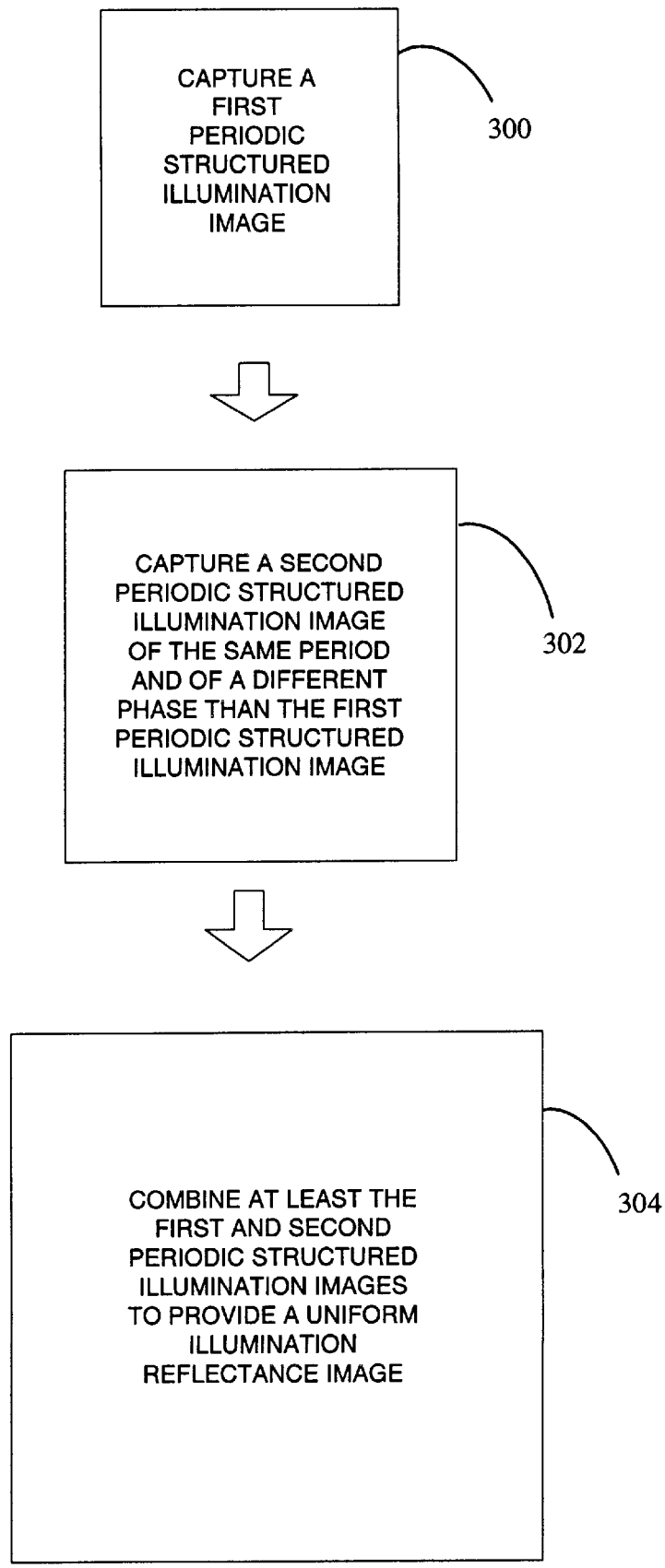
FIG. 7 is a flow diagram of the method of the invention.

Referring to FIG. 7, the method of the invention provides a uniform-illumination reflectance image, in a system employing periodic structured illumination, that is characterized by both substantial geometric correspondence and substantial photometric correspondence with at least one captured periodic structured illumination image. The method first generally employs the step of capturing a first periodic structured illumination image of the object (300) to provide a first captured periodic structured illumination image characterized by a period and a first phase. Next; a second periodic structured illumination image of the object is captured (302) so as to provide a second captured periodic structured illumination image characterized by a second phase and by a period that is substantially identical to the period of the first captured periodic structured illumination image. Then, at least the first captured periodic structured illumination image and the second captured periodic structured illumination image are combined (304) so as to provide a substantially uniform-illumination reflectance image that is characterized by both substantial geometric correspondence with at least one of the captured periodic structured illumination images, and substantial photometric correspondence with the at least one of the captured periodic structured illumination images. In general, where the spanning set of periodic structured illumination images has more than two members, the second phase is different from the first phase. When there are only two periodic structured illumination images, it is preferable that the second phase is in 180 degree phase relationship with the first phase.

Other modifications and implementations will occur to those skilled in the art without departing from the spirit and the scope of the invention as claimed. Accordingly, the above description is not intended to limit the invention except as indicated in the following claims.

What is claimed is:

1. A method for forming a uniform-illumination reflectance image of an object in a system employing periodic structured illumination, the uniform-illumination reflectance image being characterized by both substantial geometric correspondence and substantial photometric correspondence with at least one captured periodic structured illumination image, the method comprising the steps of:

capturing a first periodic structured illumination image of the object to provide a first captured periodic structured illumination image characterized by a period and a first phase;

capturing a second periodic structured illumination image of the object to provide a second captured periodic structured illumination image characterized by a second phase and by a period that is substantially identical to the period of the first captured periodic structured illumination image; and combining at least the first captured periodic structured illumination image with the second captured periodic structured illumination image so as to provide a substantially uniform-illumination reflectance image characterized by both substantial geometric correspondence with at least one of the captured periodic structured illumination images, and substantial photometric correspondence with said at least one of the captured periodic structured illumination images.

2. The method of claim 1, wherein the second phase is in 180 degree phase relationship with the first phase.

3. The method of claim 1, wherein the second phase is different from the first phase.

4. The method of claim 1, wherein only two periodic structured illumination images of the object are combined to provide the uniform-illumination reflectance image of the object.

5. The method of claim 1, wherein the step of capturing a second periodic structured illumination image of the object includes the step of:

shifting a structured illumination mask.

6. The method of claim 5, wherein the structured illumination mask is physically shifted.

7. The method of claim 5, wherein the structured illumination mask is electronically shifted.

8. The method of claim 1, wherein the step of capturing a second periodic structured illumination image of the object includes the step of:

shifting the object.

9. The method of claim 1, wherein the step of capturing a second periodic structured illumination image of the object includes the step of:

optically steering rays that together project the periodic structured illumination.

10. The method of claim 9, wherein the step of optically steering is accomplished by the steps of:

transmitting the rays through a transparent plate; and tilting the transparent plate.

11. The method of claim 1, wherein said first and second periodic structured illumination images are striped images.

12. The method of claim 1, wherein said first and second periodic structured illumination images are two-dimensional periodic array images.

13. An apparatus for forming a uniform-illumination reflectance image of an object in a system employing periodic structured illumination, the uniform-illumination reflectance image being characterized by both substantial geometric correspondence and substantial photometric correspondence with at least one captured periodic structured illumination image, the apparatus comprising:

means for capturing a first periodic structured illumination image of the object to provide a first captured periodic structured illumination image characterized by a period and a first phase;

means for capturing a second periodic structured illumination image of the object to provide a second captured periodic structured illumination image characterized by a second phase and by a period that is substantially identical to the period of the first captured periodic structured illumination image; and image combination means, cooperative with said means for capturing said first periodic structured illumination image and said second structured illumination image, for combining at least the first captured periodic structured illumination image with the second captured periodic structured illumination image so as to provide a substantially uniform-illumination reflectance image characterized by both substantial geometric correspondence with at least one of the captured periodic structured illumination images, and substantial photometric correspondence with said at least one of the captured periodic structured illumination images.

14. The apparatus of claim 13, wherein the second phase is in 180 degree phase relationship with the first phase.

15. The apparatus of claim 13, wherein the second phase is different from the first phase.

16. The apparatus of claim 13, wherein only two periodic structured illumination images of the object are combined to provide the uniform-illumination reflectance image of the object.

17. The apparatus of claim 13, wherein the means for capturing a second periodic structured illumination image of the object includes:

means for physically shifting a structured illumination mask.

18. The apparatus of claim 13, wherein the means for capturing a second periodic structured illumination image of the object includes:

means for electronically shifting a structured illumination mask.

19. The apparatus of claim 13, wherein the means for capturing a second periodic structured illumination image of the object includes:

means for shifting the object.

20. The apparatus of claim 13, wherein the means for capturing a second periodic structured illumination image of the object includes:

means for optically steering rays that together project the periodic structured illumination.

21. The apparatus of claim 20, wherein the means for optically steering rays includes:

a transparent plate; and means for tilting the transparent plate.

22. The apparatus of claim 13, wherein the first and second periodic structured illumination images are stripped images.

23. The apparatus of claim 13, wherein the first and second periodic structured illumination images are two-dimensional periodic array images.

24. An apparatus for forming a uniform-illumination reflectance image of an object in a system employing periodic structured illumination, the uniform-illumination reflectance image being characterized by both substantial geometric correspondence and substantial photometric correspondence with at least one captured periodic structured illumination image, the apparatus comprising:

an illumination assembly, including a periodic structured illumination mask;

a viewing assembly, optically coaxial with respect to the illumination assembly, for forming a plurality of periodic structured illumination images;

an image capture module, cooperative with the viewing assembly;

a processor, cooperative with the image capture module, for combining the plurality of periodic structured illumination images to provide a uniform illumination reflectance image.

25. The apparatus of claim 24, further comprising:

an actuator, controlled by the processor, for facilitating the forming of the plurality of periodic structured illumination images.

26. The apparatus of claim 24, wherein said illumination assembly includes:

a tiltable transparent plate, the plate being moveable by the actuator.

27. The apparatus of claim 25, wherein the illumination assembly further comprises:

a moveable mask carriage for moveably supporting the periodic structured illumination mask, the moveable mask carriage being moved by the actuator.

28. The apparatus of claim 25, further comprising:

a motion stage for moveably supporting the object, the motion stage being moved by the actuator.

\* \* \* \* \*